United States Patent
Pinsky

(10) Patent No.: US 12,280,129 B2
(45) Date of Patent: Apr. 22, 2025

(54) COMPOSITIONS AND METHODS FOR IMPROVED SKIN CARE

(71) Applicant: Mark A. Pinsky, Palm Beach Gardens, FL (US)

(72) Inventor: Mark A. Pinsky, Palm Beach Gardens, FL (US)

(*) Notice: Subject to any disclaimer, the term of this patent is extended or adjusted under 35 U.S.C. 154(b) by 677 days.

(21) Appl. No.: 17/360,537

(22) Filed: Jun. 28, 2021

(65) Prior Publication Data
US 2022/0117863 A1    Apr. 21, 2022

Related U.S. Application Data

(63) Continuation of application No. 16/390,604, filed on Apr. 22, 2019, now abandoned, which is a continuation of application No. 15/692,708, filed on Aug. 31, 2017, now abandoned, which is a continuation of application No. 14/080,883, filed on Nov. 15, 2013, now abandoned, which is a continuation of application No. 12/780,320, filed on May 14, 2010, now abandoned, which is a continuation of application No. 11/542,554, filed on Oct. 3, 2006, now abandoned.

(60) Provisional application No. 60/833,045, filed on Jul. 25, 2006, provisional application No. 60/723,043, filed on Oct. 3, 2005.

(51) Int. Cl.
| | |
|---|---|
| *A61K 9/127* | (2006.01) |
| *A61K 8/14* | (2006.01) |
| *A61K 8/65* | (2006.01) |
| *A61K 8/73* | (2006.01) |
| *A61K 9/00* | (2006.01) |
| *A61K 9/1272* | (2025.01) |
| *A61K 31/728* | (2006.01) |
| *A61K 38/39* | (2006.01) |
| *A61K 47/36* | (2006.01) |
| *A61K 47/42* | (2017.01) |
| *A61Q 19/00* | (2006.01) |
| *A61Q 19/02* | (2006.01) |
| *A61Q 19/04* | (2006.01) |
| *A61Q 19/08* | (2006.01) |

(52) U.S. Cl.
CPC .............. *A61K 8/14* (2013.01); *A61K 8/65* (2013.01); *A61K 8/735* (2013.01); *A61K 9/0014* (2013.01); *A61K 9/127* (2013.01); *A61K 9/1272* (2013.01); *A61K 31/728* (2013.01); *A61K 38/39* (2013.01); *A61K 47/36* (2013.01); *A61K 47/42* (2013.01); *A61Q 19/00* (2013.01); *A61Q 19/02* (2013.01); *A61Q 19/04* (2013.01); *A61Q 19/08* (2013.01)

(58) Field of Classification Search
None
See application file for complete search history.

(56) References Cited

U.S. PATENT DOCUMENTS

| | | |
|---|---|---|
| 4,186,183 A | 1/1980 | Steck et al. |
| 4,830,857 A | 5/1989 | Handjani et al. |
| 4,855,090 A | 8/1989 | Wallach |
| 4,911,928 A | 3/1990 | Wallach |
| 4,919,841 A | 4/1990 | Kamel et al. |
| 5,188,837 A | 2/1993 | Domb |
| 5,256,422 A | 10/1993 | Albert et al. |
| 5,354,564 A | 10/1994 | Borish |
| 5,358,752 A | 10/1994 | Evans et al. |
| 5,474,848 A | 12/1995 | Wallach |
| 5,603,872 A | 5/1997 | Margalit |
| 5,628,936 A | 5/1997 | Wallach |
| 5,643,600 A | 7/1997 | Marthur |
| 5,643,601 A | 7/1997 | Gross et al. |
| 5,660,839 A | 8/1997 | Allec et al. |
| 5,667,800 A | 9/1997 | De Vringer |
| 5,672,336 A | 9/1997 | Sharma |
| 5,759,526 A | 6/1998 | Simonnet et al. |
| 5,780,060 A | 7/1998 | Levy et al. |
| 5,846,561 A | 12/1998 | Margalit |
| 5,851,517 A | 12/1998 | Mougin et al. |
| 5,919,487 A | 7/1999 | Simonnet et al. |
| 5,945,095 A | 8/1999 | Mougin et al. |
| 6,068,834 A | 6/2000 | Kvalnes et al. |
| 6,127,523 A | 10/2000 | Brewton |
| 6,387,373 B1 | 5/2002 | Wright et al. |
| 6,451,338 B1 | 9/2002 | Gregoriadis et al. |
| 6,548,047 B1 | 4/2003 | Unger |
| 6,733,776 B1 | 5/2004 | Li et al. |
| 2001/0041684 A1 | 11/2001 | Lezdey et al. |
| 2002/0143171 A1 | 10/2002 | Yui et al. |

(Continued)

FOREIGN PATENT DOCUMENTS

| | | |
|---|---|---|
| CA | 2138977 | 5/1999 |
| CA | 2097801 C | 1/2002 |

(Continued)

OTHER PUBLICATIONS

Gupta, R. et al., "Adjuvant properties of non-phospholipid liposomes (Novasomes®) in experimental animals for human vaccine antigens," Vaccine, 1996, pp. 219-225, vol. 14, No. 3.

Holick, M.F. et al., "Topical PTH (1-34) is a novel, safe and effective treatment for psoriasis: a randomized self-controlled trial and an open trial," British Journal of Dermatology, 2003, pp. 370-376, vol. 149.

Kim, S., "Preparation of cell-size unilamellar liposomes with high captured vol. and defined size distribution," Biochim Biophys Acta., 1981, pp. 1-9, vol. 646.

(Continued)

*Primary Examiner* — Brian Gulledge
(74) *Attorney, Agent, or Firm* — SALIWANCHIK, LLOYD & EISENSCHENK

(57) ABSTRACT

Compositions and methods for administering collagen to a human subject have been developed. The collagen-containing lipid vesicles of the invention provide a delivery system for human collagen which eliminates problems associated with chemical and physical instability of the collagen as well as immune responses to non-human collagen.

7 Claims, No Drawings

(56) References Cited

U.S. PATENT DOCUMENTS

| | | | |
|---|---|---|---|
| 2004/0018592 A1 | 1/2004 | Bell et al. | |
| 2004/0120913 A1 | 6/2004 | Shah et al. | |
| 2005/0123593 A1 | 6/2005 | Thompson | |
| 2008/0188441 A1 | 8/2008 | Reinmuller | |

FOREIGN PATENT DOCUMENTS

| | | |
|---|---|---|
| CA | 2451245 | 1/2003 |
| CA | 2608811 | 11/2006 |
| EP | 0467795 | 1/1992 |
| EP | 0474270 | 11/1992 |
| EP | 0992236 | 12/2000 |
| EP | 1391509 | 2/2004 |
| EP | 1698696 | 6/2006 |
| JP | 04029915 | 1/1992 |
| JP | 04505774 | 10/1992 |
| JP | 05286824 | 2/1993 |
| JP | H6503259 | 4/1994 |
| JP | 06166616 | 6/1994 |
| JP | 06321731 | 7/1994 |
| JP | 07291853 | 7/1995 |
| JP | 07508008 | 7/1995 |
| JP | 09512284 | 12/1997 |
| JP | 11001423 | 1/1999 |
| JP | 11130615 | 5/1999 |
| JP | 01513509 | 9/2001 |
| JP | 02145721 | 5/2002 |
| JP | 02338483 | 11/2002 |
| JP | 02356501 | 12/2002 |
| JP | 03342147 | 3/2003 |
| JP | 2004507588 | 3/2004 |
| KR | 0107609 | 11/1996 |
| WO | 9104279 | 4/1991 |
| WO | 9214447 | 9/1992 |
| WO | 9400098 | 1/1994 |
| WO | 9610394 | 4/1996 |
| WO | 9625142 | 8/1996 |
| WO | 9907397 | 2/1999 |
| WO | 0018371 | 4/2000 |
| WO | 0103669 | 3/2001 |
| WO | 0139815 | 6/2001 |
| WO | 0172283 | 10/2001 |
| WO | 0218450 | 3/2002 |
| WO | 03000190 | 1/2003 |
| WO | 2003000191 | 1/2003 |
| WO | 2005053643 | 6/2005 |
| WO | 2006122638 | 6/2005 |

OTHER PUBLICATIONS

Morello, Peter et al., "Preparation and characterization of poly(methyl methacrylate)-iron(III) oxide mircoparticles using a modified solvent evaporation method", Journal of Microencapsulation, Aug. 2007, p. 476-491, vol. 24, No. 5, Taylor & Francis, United States.

Niemiec S. et al., "Influence of Nonionic Liposomal Composition on Topical Delivery of Peptide Drugs into Pilosebaceous Units: An in vivo Study Using the Hamster Ear Model," Pharmaceutical Research, 1995, pp. 1184-1188, vol. 12, No. 8.

COMPOSITIONS AND METHODS FOR IMPROVED SKIN CARE

CROSS-REFERENCE TO RELATED APPLICATION(S)

This application is a continuation of co-pending application Ser. No. 16/390,604, filed Apr. 22, 2019; which is a continuation of application Ser. No. 15/692,708, filed Aug. 31, 2017; which is a continuation of Ser. No. 14/080,883, filed Nov. 15, 2013; which is a continuation application of Ser. No. 14/780,320, filed May 14, 2010; which is a continuation application of Ser. No. 11/542,554, filed Oct. 3, 2006; which claims the benefit of provisional patent application Ser. No. 60/723,043, filed Oct. 3, 2005; and Ser. No. 60/833,045, filed Jul. 25, 2006, all of which are hereby incorporated by reference in their entirety, including any figures, tables, or drawings.

BACKGROUND OF THE INVENTION

The skin is the largest organ in the human body and consists essentially of two primary layers—the epidermis and the dermis. The epidermis is the outermost layer and, among other things, controls water loss from cells and tissue. The dermis is the layer below the epidermis and contains blood vessels, lymph vessels, hair follicles and sweat glands. Below the dermis is the hypodermis. Although the hypodermis is considered to be part of the integumentary system, it is not generally considered to be a layer of the skin. The hypodermis is used mainly for fat storage.

The outermost epidermis is made up of stratified squamous epithelium with an underlying basement membrane. It contains no blood vessels, and is nourished by diffusion from the dermis. The main type of cells that make up the epidermis are keratinocytes, with melanocytes and Langerhans cells also present. The epidermis can be further subdivided into the following strata (beginning with the outermost layer): corneum, lucidum, granulosum, spinosum, basale. Cells are formed through mitosis at the innermost layers. They move up the strata changing shape and composition as they differentiate and become filled with keratin. They eventually reach the corneum and become sloughed off. This process is called keratinization and takes place within about 30 days.

The dermis consists largely of the protein collagen, which forms a network of cross-linked fibers providing a framework for blood vessels and cell growth. Because it is the primary component of the dermis, collagen acts as the support structure for the skin. The health and stability of collagen is a critical factor in determining the contour, wrinkles and lines in the skin.

Hyaluronic acid (HA) is a natural substance found in all living organisms in soft connective tissues, the vitreous humor of the eye, some cartilage and joint fluids, and skin tissue. In skin tissue, hyaluronic acid is a jelly like substance that fills the space between collagen and elastin fibers. Its role is to provide a mechanism of transport of essential nutrients from the bloodstream to living skin cells, to hydrate the skin by holding in water, and to act as a cushioning and lubricating agent against mechanical and chemical damage. Over time however, due to aging and other external factors, the body's natural supply of hyaluronic acid is slowly absorbed and disappears gradually.

There are 7 to 8 grams of hyaluronic acid in adults, 50% of which (3.5-4.0 g) are found in the skin. It is distributed at approximately 0.5 mg/g in the dermis and about 0.1 mg/g in the epidermis. It is not specific to species or organs and is thought to be without risk of promoting allergy or causing a foreign body reaction.

Administration of hyaluronic acid can be used to help hydrate the skin, smooth wrinkles, and generally improve skin appearance. The effectiveness of such administration is limited by the relatively rapid breakdown of this compound caused by enzymes that exist naturally in the body. In recent years, efforts have been made to create longer lasting hyaluronic acid compositions. Specifically, cross-linked hyaluronic acid compounds have now been developed that significantly increase the half-life of HA in the body. These compositions, which have reduced water solubility, are injected for cosmetic treatment. These injections are similar to collagen injections and, apart from being non-allergenic, have the same limitations and drawbacks. These limitations and drawbacks are discussed in more detail below.

Collagen, a naturally occurring fibrous protein found in both humans and animals, provides structural support for bones, tendons, ligaments, and blood vessels, in addition to its role in the skin. Collagen is the most abundant protein in the body.

There are several major types of collagen, which give rise to the variety of structural and functional properties that collagen exhibits throughout the body. With age or injury, the collagen in a person begins to weaken and lose its elasticity. In the skin, this process eventually results in the appearance of wrinkles.

The basic structural unit of a collagen fiber is tropocollagen. It consists of a triple helix of three intertwined peptide chains of approximately 1000 amino acid residues. The basic polypeptide unit of the peptide chain is a repeating sequence of 3 amino acids, where every third residue is a glycine, and the other two alternate between proline and hydroproline. It is important to the stabilizing feature of the collagen fiber that the glycine residue is every third residue because its small side chain allows for tight coiling of the three helices, providing a strong stabilizing structure.

In young skin, the collagen remains intact and elastic, however, as the skin ages, the support structure weakens, the skin loses elasticity and the collagen support wears down from the cumulative stress of, for example, facial expressions. This causes lines and wrinkles to appear in the skin.

Collagen replacement therapy can be used to treat conditions associated with the breakdown or loss of collagen. For example, skin wrinkles can be treated by injecting highly purified collagen into the dermis. Injection of collagen has also been used to soften scar tissue and create fuller lips.

Current collagen replacement therapies include collagen injections in which purified animal collagen is used to replace lost tissue. Zyderm® and Zyplast® are bovine collagen implants that are injected into the dermis. There they become incorporated into the human collagen framework and replenish the skin's natural collagen thereby restoring the support structure and the contour of the skin. This injection therapy enhances and improves the natural appearance of skin and smoothes facial lines and scars.

Procedures involving injecting collagen are not without risk. For example, bovine collagen injections can cause allergic reactions such as redness, swelling, firmness, itching and, in rare instances, abscess formation. Worse, some physicians have reported the occurrence of connective tissue diseases such as rheumatoid arthritis, systemic lupus erythematosus, dermatomyositis (DM), and polymyositis (PM) subsequent to collagen injections in patients with no previous history of these disorders.

Also, the injection process itself poses certain challenges. For example, the practitioner injecting collagen (and/or hyaluronic acid) must control the depth, orientation and position of the needle at a particular injection site, while providing an inward force on the plunger that is sufficient to force a controlled flow rate of high viscosity collagen out of the needle and into the exact location in the dermis that will provide the desired cosmetic effect. The locating of the needle tip at the proper depth within the dermis is also difficult for the practitioner. To engage the tip of the needle at the proper injection depth, the practitioner may move the needle inwardly and outwardly with respect to the surface of the skin (epidermis). However, there is no visual reference point, other than the end of the syringe body, from which the practitioner can easily determine the extent that the needle extends into the dermis. Thus, the needle tip may be placed too deep, or too shallow, for the intended application. It should be appreciated that the person (practitioner) injecting the collagen must have good, steady control of the fingers, hand and arm and also have excellent eye-hand coordination to be an effective provider of cosmetic collagen injections. These qualities are not always present in individuals, and this has limited the availability of collagen therapy to patients.

In addition to injection, collagen may be delivered to the skin by topical application. Unfortunately, such topical collagen therapy has proven less than effective as conventional forms of collagen do not appear to penetrate into the dermis. As noted above, the skin consists of multiple layers and is extremely complex in terms of its function as well as its chemical make-up. Transdermal (through the skin) application of medicines and other substances poses a wide range of formulation hurdles. The ability to deliver desired substances to a layer within the skin is equally, if not even more, difficult.

Various means for delivery of substances to or into the skin have been proposed.

U.S. Pat. No. 5,354,564 discloses personal care products comprising an aqueous dispersion of particles of silicone wherein said particles have a surface modifier adsorbed on the surface thereof in an amount sufficient to achieve a particle size of less than about 400 nanometers (nm).

U.S. Pat. No. 5,660,839 discloses incorporating deformable hollow particles into cosmetic and/or dermatological compositions containing fatty substances, for markedly reduce or eliminate the sticky and/or greasy feel attributed to these fatty substances.

U.S. Pat. No. 5,667,800 discloses an aqueous suspension of solid lipid nanoparticles, comprising at least one lipid and preferably also at least one emulsifier, for topical application to the body.

U.S. Pat. No. 5,780,060 discloses microcapsules with a wall of crosslinked plant polyphenols and compositions containing them. The microcapsules are obtained by the interfacial crosslinking of plant polyphenols, particularly flavonoids.

U.S. Pat. Nos. 5,851,517 and 5,945,095 disclose compositions including a dispersion of polymer particles in a non-aqueous medium. A dispersion of surface-stabilized polymer particles can be used in a non-aqueous medium, in a cosmetic, hygiene or pharmaceutical composition. The dispersions may, in particular, be in the form of nano-particles of polymers in stable dispersion in a non-aqueous medium.

U.S. Pat. Nos. 5,759,526 and 5,919,487 disclose nanoparticles coated with a lamellar phase based on silicone surfactant and compositions containing them. The nanoparticles, and in particular nanocapsules, provided with a lamellar coating obtained from a silicone surfactant, can be used in a composition, in particular a topical composition, for treatment of the skin, mucosae, nails, scalp and/or hair.

U.S. Pat. No. 5,188,837 discloses a microsuspension system and method for its preparation. The microsuspension contains liposphers which are solid, water-insoluble microparticles that have a layer of a phospholipid embedded on their surface. The core of the liposphere is a solid substance to be delivered or a substance to be delivered that is dispersed in an inert solid vehicle such as a wax.

U.S. Pat. No. 4,919,841 discloses a process for preparing encapsulated active particles by the steps of: dispersing active materials in molten wax; emulsifying the active/wax dispersion in an aqueous surfactant solution for no longer than 4 minutes; quenching the capsules by cooling; and retrieving solidified capsules. Examples of active materials are fragrances.

Each of these methods has disadvantages, particularly with respect to the delivery of collagen and/or hyaluronic acid.

Liposomes are vesicular lipid membrane structures that enclose, for example, a volume of water. The existence of liposomes has been known for many years. In the early 1900's, researchers, studying isolated lecithin (phosphatidylcholine), cephalin (phosphatidylethanolamine/phosphatidylserine), phrenosin (galactosyl ceramide) and kerasin (glucosyl ceramide), found that all of these molecules would swell in water to form hydrated multilamellar layers, consisting of lipid bilayers separated by water. Also, mixtures of ionic and nonionic lipids dispersed in water were found to form stable "emulsions" in which the lipid molecules take up positions side by side to form a homogeneous mixed phase. These emulsions were the equivalents of what are now called multilamellar liposomes.

Physical and chemical studies have shown that amphiphiles form certain preferred arrays in the presence of water. Formation of these arrays, which include micelles, monolayers and bimolecular layers, is driven by the need for the polar head groups, which may be ionogenic or not, to associate with water and the need of the apolar, hydrophobic tail to be excluded from water. Exactly which type of structure is assumed depends upon the nature of the amphiphile, its concentration, the presence of other amphiphiles, temperature, and presence of salt and other solutes in the aqueous phase.

Until recently, liposome technology has been concerned mostly with vesicles composed of phospholipids, predominantly phosphatidylcholine, and these continue to be the focus of most publications and patents. However, although phospholipids are suitable for certain pharmaceutical applications, phospholipid liposome technology has been beset by serious problems, for example, phospholipids turn over rapidly in vivo and are unstable in storage. Also, they are labile and expensive to purify or synthesize, and the manufacture of phospholipid liposomes is difficult and costly to scale up.

Although liposomes are well known in the art, there are no previous reports of their use to efficiently deliver collagen and/or hyaluronic acid in a skin care formulation.

BRIEF SUMMARY OF THE INVENTION

The subject invention pertains to new and advantageous skin care compositions. In a preferred embodiment, the subject invention provides lipid vesicles (liposomes) incorporating hyaluronic acid. Particularly preferred is the use of cross-linked hyaluronic acid. Free, or non-crosslinked hyaluronic acid may also be used as a component of the composition. In a further preferred embodiment, the compositions of the subject invention also comprise vesicles containing collagen. The compositions may also contain additional skin care agents.

The subject invention further pertains to methods of using such lipid vesicles for delivery of hyaluronic acid, collagen, and other active ingredients to a patient to achieve enhanced skin care.

Hyaluronic acid is a naturally occurring sugar that exists in all living organisms and is a universal component of the extra-cellular spaces of body tissues. It functions by holding together collagen and elastin, thus providing a framework for the skin. When applied to the skin according to the subject invention, preferably in cross-linked gel form, hyaluronic acid acts as a dermal filler by binding to water and providing volume to easily fill in facial lines and cause visible plumping of the skin. When used according to the subject invention hyaluronic acid acts as an efficient hydrating agent.

In one embodiment, the present invention provides a skin care composition with cross-linked hyaluronic acid that further comprises a safe and effective amount of collagen, wherein the formulation facilitates the active ingredients passing through the epidermis and thus being released within the dermis of the skin. In a further embodiment, the human collagen and/or crosslinked HA may be delivered to the epidermis as well. Accordingly, the present invention is useful in regulating and/or improving the condition of the skin (including the appearance and/or feel of the skin) by efficiently delivering hyaluronic acid and/or collagen to the appropriate location within the skin.

In addition, the use of human collagen (e.g., recombinant human collagen or human collagen isolated from human tissue or cultured human fibroblasts), or a fragment thereof, is advantageous for avoiding undesired side effects such as allergic or autoimmune reactions. Advantageously, hyaluronic acid does not present a significant risk of an allergic reaction.

The present invention also relates to methods of using such compositions to regulate and/or improve the condition of skin. The methods of the subject invention generally include the step of topically applying the compositions to the skin (epidermis) of the patient needing such treatment, wherein a therapeutically effective amount of such composition is applied.

Advantageously, the present invention provides compositions and methods for combating the aging of skin, wherein combating the aging of skin can include, for example, hydration of the skin, treating the appearance of wrinkles, fine lines, and other forms of undesirable skin texture. By presenting collagen and/or hyaluronic acid into the dermal and/or epidermal layer(s) of the skin, the form, strength, as well as function of the skin is enhanced.

In certain embodiments, the compositions of the subject invention comprise a dispersion of lipid vesicles that contain agents, in addition to hyaluronic acid and collagen, that are useful in delaying, minimizing, or eliminating skin aging, wrinkling, and/or other histological changes typically associated with the intrinsic conditions (such as aging, menopause, acne, etc.) and extrinsic conditions (such as environmental pollution, wind, heat, low humidity, harsh surfactants, etc.).

In an exemplary embodiment of the invention non-phospholipid paucilamellar lipid vesicles incorporating human collagen and hyaluronic acid are used to deliver collagen to the skin of a human subject. Non-phospholipid paucilamellar lipid vesicles are particularly advantageous for use in the invention as such vesicles are stable and inexpensive to manufacture, and also feature a large cavity size for holding collagen. In an alternative embodiment, cyclodextrins are used to deliver the active agents to the dermis layer of the skin.

DETAILED DESCRIPTION

The present invention is directed to materials and methods for the topical administration of a therapeutically effective amount of hyaluronic acid and/or collagen to a specific layer within the skin in order to improve the condition of the skin. Accordingly, in a preferred embodiment, the present invention provides compositions, and methods for using such compositions, comprising a dispersion of lipid vesicles that contain at least hyaluronic acid and/or collagen (and, optionally, other skin care agents), wherein the lipid vesicles facilitate penetration through the epidermis and dispersal of the vesicle contents, into the dermis layer of the skin.

Improvement of skin condition is often desired due to conditions that may be induced or caused by factors internal and/or external to the body. Examples include, but are not limited to, environmental damage, smoking, radiation exposure (including ultraviolet radiation), chronological aging, menopausal status (e.g., post-menopausal changes in skin), stress, diseases, etc.

The present invention is useful for therapeutically and/or prophylactically improving visible and/or tactile characteristics in skin. For example, in one embodiment, the length, depth, and/or other dimension of lines and/or wrinkles are decreased and hydration is achieved.

"Improving skin condition" includes prophylactically preventing or therapeutically treating a skin condition, and may involve one or more of the following benefits: thickening of skin, preventing loss of skin elasticity, and a reduction in lines or winkles.

Following are additional definitions relevant to the subject invention. It should be appreciated that the following definitions are used throughout this application. Unless otherwise defined, all technical terms used herein have the same meaning as commonly understood by one or ordinary skill in the art to which this invention belongs.

The term "epidermis" or "epidermal," as used herein, refers to the outermost layer of the skin.

The term "topical application," as used herein, means to apply or spread the compositions of the present invention onto the surface of the epidermis tissue.

The term "dermatologically-acceptable," as used herein, means that the compositions or components thereof so described are suitable for use in contact with mammalian epidermal tissue without undue toxicity, incompatibility, instability, allergic response, and the like.

The term "therapeutically effective amount," as used herein, refers to an amount of a compound (such as collagen) or composition sufficient to induce a positive benefit, preferably a positive skin appearance and/or feel. In accordance with the subject invention, the therapeutically effective amount is an amount of collagen, either alone or in combination with other agents, that regulates and/or improves the skin, but where the amount is low enough to avoid serious side effects, i.e., to provide a reasonable benefit to risk ratio, within the scope of sound judgment of the skilled artisan.

The term "sagging" as used herein means the laxity, slackness, or the like condition of skin that occurs as a result of loss of, damage to, alterations to, and/or abnormalities in dermal structure and/or function.

The terms "smoothing" and "softening," as used herein, refer to altering the surface of the epidermis tissue such that its tactile feel is improved.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles and coarse deep wrinkles, skin lines, crevices, bumps, large pores (e.g., associated with adnexal structures such as sweat gland ducts, sebaceous glands, or hair follicles), or unevenness or roughness, loss of skin elasticity, sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

As used herein, "shear mixing" means the mixing of a lipophilic phase with an aqueous phase under turbulent or shear conditions that provide adequate mixing to hydrate the lipid and form lipid vesicles By the terms "disperse" and "dispersion" are meant dissolution or forming a suspension or colloid to yield a flowable phase.

As used herein, a "nucleic acid" or a "nucleic acid molecule" means a chain of two or more nucleotides such as RNA (ribonucleic acid) and DNA (deoxyribonucleic acid). A "recombinant" nucleic acid molecule is one made by an artificial combination of two otherwise separated segments of sequence, e.g., by chemical synthesis or by the manipulation of isolated segments of nucleic acids by genetic engineering techniques.

The terms "protein" and "polypeptide" are used synonymously to mean any peptide-linked chain of amino acids, regardless of length or post-translational modification, e.g., glycosylation or phosphorylation. A "purified" polypeptide is one that has been substantially separated or isolated away from other polypeptides in a cell or organism in which the polypeptide naturally occurs (e.g., 90, 95, 98, 99, 100% free of contaminants).

When referring to a nucleic acid or polypeptide, the term "native" refers to a naturally-occurring nucleic acid or polypeptide.

The compositions of the present invention, which enable dermal layer dispersion of collagen, are useful for improving the skin, including improving skin appearance and/or feel. For example, compositions of the present invention are useful for improving the appearance of skin condition by providing a visual improvement in skin appearance following application of the composition to the skin.

Advantageously, the compositions of the present invention may have additional desirable properties, including stability, long shelf-life, absence of significant skin irritation, and good aesthetics. In certain embodiments, to accomplish such additional benefits, the compositions of the invention further comprise agents, in addition to the collagen, that promote composition stability, reduce skin irritation, and/or enhance the aesthetic appeal of the composition.

Examples of good aesthetics include compositions, such as luxurious creams and lotions, that (i) are light and nongreasy, (ii) have a smooth, silky feel upon the skin, (iii) spread easily, and/or (iv) absorb quickly. Other examples of good aesthetics include compositions that have a consumer acceptable appearance (i.e. no unpleasant odor or discoloration present), and provide good skin feel.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the particular embodiments discussed below are illustrative only and not intended to be limiting.

Hyaluronic Acid

Hyaluronic acid (HA) is present throughout nature and is a combination of repeated disaccharide units of glucuronic acid and N-acetyl glucosamine. It is polyionic and has an axial hydrophobic part and a central hydrophilic part. Hyaluronic acid is very sensitive to hyaluronidases and, therefore, has a short half-life in the body. In order to make it a wrinkle-filling product that has sufficient sustainability over time it can be cross-linked.

Numerous substances can be used to cross-link hyaluronic acid including formaldehyde, epoxides, polyaziridyl compounds, divinyl sulfone and others. One cross-linking agent is divinyl sulfone. This substance reacts readily with hyaluronic acid in aqueous alkaline solutions, thereby providing cross-linked HA gels. These gels swell in water. The swelling ratio depends upon the degree of cross-linking of the gel. The degree of cross-linking can be controlled by changing several factors including the molecular weight of the HA, its concentration in the reaction mixture, the alkali concentration and the polymer/DVS ratio. The swelling ratio of these gels can be from 20 up to 8000, and more, depending upon the reaction parameters.

An even more preferred cross-linking agent is 1,4-butanediol diglycidyl ether (BDDE).

The swelling ratio of cross-linked HA gels is substantially greater than the swelling ratio of cross-linked gels of other polysaccharides obtained under the same reaction conditions. This can probably be explained by the unique nature of HA (as compared to other polysaccharides) and its water solutions. In water, a large molecule of HA forms a very flexible, long random coil that takes up a large volume in the solution.

The unique property of HA to give highly swollen cross-linked gels can be used to effect modification of the properties of cross-linked gels made of mixtures of HA with other hydrophilic polymers. These polymers include other polysaccharides, synthetic and natural, such as hydroxyethyl cellulose, carboxymethyl cellulose, xanthan gum, glycosaminoglycans, proteins and glyco proteins of various types, such as collagen, elastin, albumin, globulin, etc, sulfated proteins, synthetic water-soluble polymers, such as polyvinyl alcohol and its co-polymers, co-polymers of poly-(hydroxyethyl) methacrylate and the like. Any polymer soluble in water or aqueous alkaline solutions and containing groups capable of reacting with DVS, namely, hydroxyl, amino or sulfhydryl groups, can be used to obtain highly swollen cross-linked mixed gels of HA.

Another convenient method of obtaining cross-linked hyaluronic acid or mixed hyaluronic acid and other polymer gels comprises treating dry polymer preparations, i.e., in the form of a film with a cross-linking agent and subsequent swelling of the product in the desired medium.

In one embodiment, linear HA of less than 500,000 Da can be used.

As described herein, the administration of HA can be used to advantageously improve the condition of the skin. Also, because of its molecular structure, HA can be used to entrap and deliver additional active agents (drugs). There are several methods for combining a drug with the HA gel and, accordingly, several types of products that can be obtained. One of the methods comprises diffusing a drug into an HA gel when the gel is put into a solution of the drug. The product obtained by this method is a gel in which a drug substance is uniformly dispersed.

The same type of product can be obtained by dehydrating a hyaluronic acid gel and reswelling it in a drug solution. To dehydrate a gel one can use a water-miscible organic solvent or alternatively, water from a gel can be removed by drying. Preferable solvents are ethanol and isopropanol, and ketones such as acetone, though other solvents can also be used.

Yet another method can be used to obtain products of this type. This method comprises allowing a concentrated hyaluronic acid gel resulting from a cross-linking reaction previously carried out in a relatively concentrated solution of hyaluronic acid to swell in a solution of a drug substance.

Although these three methods all result in products that are essentially the same, each of the methods has certain advantages when compared to any of the other methods for any specific product and, hence, the choice of method should be made with consideration given to such parameters as nature of the drug, the desired concentration of the drug in the system, the delivery rate, etc.

A drug delivery system of another type according to the present invention is one in which a drug is covalently attached to macromolecules of hyaluronic acid and/or other polymers forming a gel. These systems are characterized by a substantially slower rate of delivery than those described above. Delivery of a drug from these systems occurs when the gel is degraded in the living body. The degradation process is usually slower than diffusion. The rate of the degradation process can be controlled by several means, including adjusting the density of the cross-links in the gel or by co-cross-linking hyaluronic acid with polymers which can be degraded in the body more easily than hyaluronic acid, e.g., proteins. By changing the concentration of such polymer components in the mixed gels, one can conveniently control their rate of degradation and, thus, the rate of drug delivery.

Another possibility of drug delivery for this type of product involves the use of such chemical bonds for attachment of a drug to polymeric molecules forming a gel that has a controllable rate of hydrolysis in a physiological environment.

To obtain this type of a product one can use a drug substance that can react with a cross-linking agent. Yet another method can be used to obtain this product. This method comprises chemically modifying a cross-linked gel after its formation, using the reactive hydroxyl groups of hyaluronic acid or the reactive groups of the polymers co-cross-linked with the hyaluronic acid to which a drug substance can be attached by numerous chemical reactions. Alternatively, additional reactive groups can be introduced by chemical treatment of a cross-linked gel which affects the macromolecules of hyaluronic acid or co-cross-linked polymers and a drug can be covalently attached to these newly formed reactive groups.

The active agents can be cosmetic, dermatological, and pharmaceutical active agents. Suitable active agents include, but are not limited to, ceramides; vitamins; antioxidants; free radical scavengers; moisturizing agents; anti-seborrhoeic agents; anti-UV agents; keratolytic agents; anti-inflammatory agents; melanoregulators; liporegulators; anti-ageing agents; antibacterial agents; agents for combating hair loss; vascular protectors; anti fungal agents; skin conditioners; immunomodulators; nutrients and essential oils; retinoids; anesthetics; preservatives; antiseptics; emollients; lubricants; humectants; pigments; dyes; hydroxy acids, such as, alpha hydroxy acids, and beta hydroxy acids; elastin; hydrolysates; epidermal growth factor; soybean saponins; and mucopolysaccharides.

Several forms of hyaluronic acid have been developed by cross-linking the acid with other natural acids or chemical compounds to form gels that improve skin condition.

At present several commercial preparations are available. These include Hylaform®, extracted from coxcomb and marketed by the Genzyme Company and Restylane® which is produced by bacteria fermentation process using *Streptococcus equi* spices and crosslinked with BDDE. These two compositions have the common feature of being biphasic injectable substances, with particles of hyaluronic acid cross-linked to a greater or lesser degree and suspended in a more fluid or even non-cross-linked preparation.

Monophasic gel preparations of hyaluronic acid are contained in other products such as Juvéderm®, Hydra Fillé and Esthélis®. As with the Restylane® each of these is produced with BDDE, although the process is different resulting in the monophasic gel.

In one embodiment, the crosslinked hyaluronic acid is produced as a monophasic composition. After linearising the spine of the native hyaluronic acid, cross-linking is started by adding BDDE. Dynamic cross-linking allows a product to be obtained that macroscopically has a homogeneous appearance, and microscopically has a heterogenous appearance. This technique allows what is called a Cohesive Polydensified Matrix to be obtained.

Placed in the presence of 1 ml of water for 2 minutes, the gel remains cohesive, which is not the case for biphasic products in which the "microparticle" component appears immediately.

This product is available under the tradename Esthe'lis®.

The visco-elastic properties of Esthe'lis® make it a substance that sculpts well in the tissue, with very gentle massage to position it correctly. It does not leave an "implanted cord" feeling and can even be referred to as having a lifting effect.

In a preferred embodiment of the subject invention, hyaluronic acid is incorporated into lipid vesicles in order to administer hyaluronic acid to the skin of a patient. As described herein, any lipid vesicle suitable for encapsulating hyaluronic acid and for administering to the skin of a human subject may be used.

Advantageously, when used according to the subject invention, this product can have a hydrating effect in the treated area with, for example, abolition of crow's feet during treatment of the eyes. The nasolabial folds are on the areas treated on the cheeks.

Collagen

The compositions of the invention can include one or more purified, or recombinant, collagens and/or collagen derivatives, or a combination thereof. Collagen proteins useful in the invention include any native collagen proteins obtained from animal (e.g., human) cells and tissue, recombinantly expressed human collagen proteins (including fragments of the full-length collagen), and combinations and/or formulations thereof.

Purified collagens for use in the methods and compositions of the invention may be isolated from animal or human tissues; however, the use of human collagen in the compositions and methods of the invention is preferred when the subject to be treated is a human in order to prevent an immune response to the collagen material. Collagen that is extracted from its source material (e.g., animal placenta, bone, hide, tendon) is typically a mixture of collagen type I with some collagen type III. Collagen material recovered from placenta, for example, is biased as to collagen type and not entirely homogenous. Techniques for isolating collagen from human placentas are described in U.S. Pat. Nos. 5,002,071 and 5,428,022.

In addition to employing collagen obtained directly from natural sources, the methods and compositions of the invention include many different types of collagen derivatives. Collagen derivatives may vary from naturally-occurring collagens in several respects. Collagen derivatives may be non-glycosylated or glycosylated differently than naturally-occurring collagens. Desired glycosylation patterns may be produced by a variety of methods, including direct chemical modification and enzymatically catalyzed glycosylation and deglycosylation reactions. Desired glycosylation patterns may also be produced by inhibiting or deleting enzymes necessary for producing the naturally-occurring glycosylation patterns found on collagens.

Collagen derivatives also include various fragments of naturally-occurring collagens. Such collagen fragments may be produced by, among other methods, chemically or enzymatically cleaving one or more peptide bonds. Collagen derivatives may also contain one or more amino acid residue differences as compared with corresponding amino acid residue positions in a naturally-occurring collagen. Collagen derivatives containing such amino acid residue substitutions may be produced by a variety of methods including genetic engineering techniques and by in vitro peptide synthesis. Additional collagen derivatives may be produced by varying the amount of hydroxylysines and/or hydroxyprolines present in a given molecule, by the varied expression of lysine hydroxylases, and/or proline hydroxylases, wherein the hydroxylase genes (recombinant or otherwise) are also expressed in a host cell for the expression of recombinant collagen, or derivatives thereof.

In certain preferred embodiments of the subject invention, pure recombinant collagen (e.g., types I or III) as opposed to the various types found in animal (e.g., bovine) collagens can be used. Pure forms of recombinant collagen have performance characteristics that in some applications are preferred to those from animal mixtures. A description of how to produce collagen types I-III by recombinant DNA technology can be found, among other places, in U.S. Pat. Nos. 5,405,757; 5,593,859; 6,617,431; 6,428,978; PCT-published patent applications WO 93/07889 and WO94/16570, and related patents and applications. The recombinant production techniques described in these references may be readily adapted so as to produce many different types of collagens, human or otherwise. Because an immune response can be elicited against non-human collagen material, human collagens produced by recombinant DNA technology are preferably used in compositions and methods of the subject invention.

A preferred collagen for use in the invention, for example, is recombinant human collagen expressed in and purified from human fibroblasts. This collagen material is produced by Inamed Corporation (Santa Barbara, CA) and is sold under the trade names CosmoDerm® and CosmoPlast®. Fibroblast cells used for culturing collagen in this method are screened for known pathogens and the resultant collagen material is tested for contaminants. Once the collagen is isolated from the cells, it is subjected to viral inactivation for increased safety. Methods for expressing recombinant genes in human fibroblasts are well known in the art.

Two additional collagen materials that are produced using recombinant DNA technology and that can be used in the invention are FG-5017 and FG-5016 (FibroGen, South San Francisco, CA). FG-5017 is made of recombinant human collagen type III formulated for safety and efficacy as an injectable gel. FG-5016 is a recombinant human collagen type III (rhCIII) developed to replace animal-derived collagen in a variety of pharmaceutical and medical device applications. FG-5016 is a highly purified and fully characterized biomaterial, which is produced using recombinant methodology in a yeast expression system free of animal components. This methodology involves the coordinate expression of genes encoding collagen and encoding prolyl 4-hydroxylase which enables formation of thermally stable, triple helical collagen.

Methods for expressing recombinant genes in yeast cells are well known in the art and are described in many references including Romanos et al., Yeast 8:423-488, 1992; Cohen et al., Nature 366: 698-701, 1993; and A. Wiseman, Genetically Engineered Proteins and Enzymes From Yeast: Production Control, 1991, Ellis Norwood Press, New York. Methods for producing triple helical collagen in yeast cells are described in U.S. Pat. No. 6,451,557. Triple helical protein products produced in the yeast cells can be purified from the cells by techniques well known in the art including standard chromatographic and precipitation techniques (See, e.g., Miller and Rhodes, Meth Enzymol., 82:33-64, 1982; and R. L. Trelstad, Native Collagen Fractionation, In: Immunochemistry of the Extracellular Matrix, vol. 1, H. Furthmayr, ed., CRC Press, Boca Raton, FL, 1982, p. 31-41).

Regardless of the collagen source, preferred collagen and collagen derivatives for use in the invention are those that are sized to fit within the lipid vesicles of the invention, e.g., less than about 800 nm. Because collagen fibrils are 20-150 nm in size, fibrils rather than fibers (which are 1000-50,000 nm) are preferred. To maintain collagen in the fibril form, the pH and/or ionic strength of the solution containing the fibrils can be appropriately manipulated. A number of methods exist to reduce collagen size, including an enzymatic breakdown using a protease. Collagen can also be broken down mechanically. For example, collagen can be processed mechanically after drying to produce fine particles that are less than 800 nm in size. Additionally, extensive hydrolysis of a collagen-containing solution may be used to prevent fiber formation.

Lipid Vesicles Containing Collagen and/or Hyaluronic Acid

The invention provides compositions including lipid vesicles incorporating human collagen (and/or a fragment thereof) or a collagen derivative, and/or hyaluronic acid. The vesicles containing the active agent(s) are useful for administering the active agent(s) to a subject. Any lipid vesicle suitable for encapsulating collagen and/or hyaluronic acid, and for administering to the skin of a human subject may be used.

Vesicles of the invention are vesicles having one or more lipid bilayer membranes surrounding a cavity. Lipid vesicles for use in the invention are typically in the range of about 50 to about 950 nm (e.g., 50, 100, 200, 300, 400, 500, 600, 700, 800, 900, 950 nm) in size. Methods for producing and using lipid vesicles are well known in the art and are described, e.g., in U.S. Pat. Nos. 4,917,951 and 5,013,497; Walde P. and Ichikawa S., Biomol Eng., 18:143-177, 2001; Hunter D. G. and Frisken B. J., Biophys J., 74:2996-3002, 1998; and Cevc G., Adv Drug Deliv Rev., 56:675-711, 2004.

Collagen to be encapsulated within lipid vesicles can be any suitable form, e.g., a preparation of collagen type I, collagen type III, a mixture of collagen type I and collagen type III, a collagen derivative, or a combination thereof.

Hyaluronic acid may be as described above. Vesicles may contain only collagen or only HA, or a combination thereof. The compositions of the subject invention may comprise vesicles that contain only one active agent, or multiple active agents.

The lipid vesicles of the invention can include non-phospholipid surfactants. They can also include a charge-producing agent and a targeting molecule. Thus, vesicles made of non-phospholipid "membrane mimetic" amphiphiles are useful in the invention. These are molecules that have a hydrophilic head group attached to a hydrophobic tail and include long-chain fatty acids, long-chain alcohols and derivatives, long-chain amino and glycerolipids. In the bilayers, the fatty acid tails point into the membrane's interior and the polar head groups point outward. The polar groups at one surface of the membrane point towards the vesicle's interior and those at the other surface point toward the external environment. As a vesicle forms during its manufacture, any water-soluble molecules that have been added to the water are incorporated into the aqueous spaces in the interior of the spheres, whereas any lipid-soluble molecules added during vesicle formation are incorporated into the core of the vesicles.

Paucilamellar vesicles that can be formed from many bio-compatible, single-tailed amphiphiles are preferred for use in the invention. Such paucilamellar lipid vesicles include non-phospholipid vesicles having one or several lipid bilayer membranes surrounding a large amorphous core in which a chemical entity of interest (i.e., collagen and/or HA) is encapsulated.

Non-phospholipid paucilamellar lipid vesicles are sold under the trade name Novasome® (IGI Inc., Buena, NJ). Several Novasome® formulations exist (e.g., Novasome® A, Novasome® D), Novasome® Day Cream).

Novasome® vesicles are useful for encapsulating chemical ingredients to aid in formulation, increase delivery to site of action and stabilize chemical ingredients in the formulation. These lipid vesicles are generally about 200-700 nanometers in size, depending upon a wide variety of membrane constituents individually chosen for each particular purpose. Their size distribution is uniform, and encapsulation efficiency can be nearly 100% for lipid cargo and 85% for aqueous materials. Finely divided insoluble particles (e.g., insoluble pharmaceuticals) can also be encapsulated.

Novasome® vesicles are inherently stable, and can be tailored to be stable at pH levels ranging from 2-13 as well as temperature ranges as low as liquid nitrogen to above the boiling point of water. They can be stable to solvents including alcohols, ethers, esters, gasoline, diesel and other fuels. They can encapsulate fragrances and flavors which contain volatile and fragile ethers, esters, aldehydes, etc. These vesicles can release their cargo under varying physical and chemical circumstances including heat, light, pH changes, enzymatic degradation, drying transmembrane diffusion, etc.

Protocols for producing and administering Novasome® formulations are described, for example, in U.S. Pat. Nos. 4,855,090; 4,911,928; 5,474,848; 5,628,936; 6,387,373; Holick et al., British Journal of Dermatology 149:1365-2133, 2003; Gupta et al., Vaccine 14:219-225, 1996; and Wallach D F H and Philippot J., New Type of Lipid Vesicle: Novasome™ In: Liposome Technology, $2^{nd}$ ed., Gregorriadis G., CRC Press, Boca Raton, FL, 1982, pp. 141-151; Niemiec et al., Pharmaceutical Research 12:1184-1188, 1995; and Alfieri D R, Cosmetic Dermatology 10:42-52, 1997.

In one embodiment, the liposomes are those used in "Day Cream."

In certain embodiments of the subject invention, the lipid vesicles (e.g., non-phospholipid paucilamellar lipid vesicles) may also include targeting molecules, either hydrophilic or amphiphilic, which can be used to direct the vesicles to a particular target in order to allow release of the HA, collagen or collagen derivative from within the vesicle at a specified biological location. If hydrophilic targeting molecules are used, they can be coupled directly or via a spacer to an OH residue of the polyoxyethylene portion of the surfactant, or they can be coupled, using techniques in the art, to molecules such as palmitic acid, long chain amines, or phosphatidyl ethanolamine. If spacers are used, the targeting molecules can be interdigitated into the hydrophilic core of the bilayer membrane via the acyl chains of these compounds. Preferred hydrophilic targeting molecules include monoclonal antibodies, other immunoglobulins, lectins, and peptide hormones.

In addition to hydrophilic targeting molecules, it is also possible to use amphiphilic targeting molecules. Amphiphilic targeting molecules are normally not chemically coupled to the surfactant molecules but rather interact with the lipophilic or hydrophobic portions of the molecules constituting the bilayer lamellae of the lipid vesicles. Preferred amphiphilic targeting molecules are neutral glycolipids, galactocerebrosides (e.g., for hepatic galactosyl receptors), or charged glycolipids such as gangliosides.

In some embodiments, charge-producing materials and steroids such as cholesterol or hydrocortisone or their analogues and derivatives are used in the formation of the lipid vesicles (e.g., paucilamellar lipid vesicles). Preferred charge-producing materials include negative charge-producing materials such as dicetyl phosphate, cetyl sulphate, phosphatidic acid, phosphatidyl serine, oleic acid, palmitic acid, or mixtures thereof. In order to provide a net positive charge to the vesicles, long chain amines, e.g., stearyl amines or oleyl amines, long chain pyridinium compounds, e.g., cetyl pyridinium chloride, quaternary ammonium compounds, or mixtures of these can be used. Another example of a positive charge-producing material is hexadecyl trimethylammonium bromide, a potent disinfectant.

Preparing Lipid Vesicles

Lipid vesicles used according to the subject invention can be any of a large variety of lipid vesicles known in the art and can be made according to any of a large number of production methods. Materials and procedures for forming lipid vesicles are well-known to those skilled in the art. In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically agent materials is then added to the film. Large multilamellar vesicles are produced upon agitation. When smaller multilamellar vesicles are desired, the larger vesicles are subjected to sonication, sequential filtration through filters with decreasing pore size or reduced by other forms of mechanical shearing. Lipid vesicles can also take the form of unilamellar vesicles, which are prepared by more extensive sonication of multilamellar vesicles, and consist of a single spherical lipid bilayer surrounding an aqueous solution. A comprehensive review of all the aforementioned lipid vesicles and methods for their preparation are described in "Liposome Technology", ed. G. Gregoriadis, CRC Press Inc., Boca Raton, Fla., Vol. I, II & III (1984). For methods of preparing lipid vesicles, also see U.S. Pat. Nos. 4,485,054, 4,761,288, 5,013,497, 5,653,996, and 6,855,296.

To prepare non-phospholipid paucilamellar lipid vesicles formed of non-phospholipid surfactant material and containing an aqueous-based collagen and/or HA material, any suitable method known in the art can be used. Methods of preparing non-phospholipid paucilamellar lipid vesicles typically involve first forming a lipophilic phase by combining several lipophilic components including surfactant material and then heating and blending this mixture. Examples of suitable surfactant materials include but are not limited to polyoxyethylene (2) cetyl ether, polyoxyethylene (4) lauryl ether, glyceryl monostearate, and poly oxyethylene (9) glyceryl stearate. The resultant lipophilic phase is then blended with an aqueous phase having an aqueous buffer and an aqueous soluble collagen formulation, under shear mixing conditions, to form the paucilamellar lipid vesicles. In this method, the temperature of the lipophilic phase is elevated in order to make it flowable followed by carrying out the shear mixing between the lipophilic phase and the aqueous phase at a temperature such that both phases are liquids. While it is often desirable to use the same temperature for both phases, this is not always necessary. Any other method known to the skilled artisan can also be used. Preferred methods for making the paucilamellar lipid vesicles of the invention are described in U.S. Pat. No. 4,911,928.

To encapsulate oil-based collagen or collagen-containing formulations within paucilamellar lipid vesicles, the collagen or collagen-containing formulation is dispersed in an oil or wax forming an oily phase. The oil or wax is a water immiscible oily solution selected from a group consisting of oils, waxes, natural and synthetic triglycerides, acyl esters, and petroleum derivatives, and their analogues and derivatives. The oily phase containing the oil-dispersible material is mixed with the lipid phase and the combined oil-lipid phase is blended under shear mixing conditions with the aqueous phase. Surfactants useful in the encapsulation process are the same as those used to make paucilamellar lipid vesicles with an aqueous core.

Paucilamellar lipid vesicles can be made by a variety of devices which provide sufficiently high shear for shear mixing. Many such devices are available on the market including a Microfluidizer® such as is made by MicroFluidics Corp. (Newton, MA), a "French"-type press, or some other device which provides a high enough shear force and the ability to handle heated, semiviscous lipids. If a very high shear device is used, it may be possible to microemulsify powdered lipids, under pressure, at a temperature below their normal melting points and still form the collagen-containing paucilamellar lipid vesicles of the present invention.

A device which is particularly useful for making the paucilamellar lipid vesicles of the present invention has been developed by Micro Vesicular Systems, Inc., (Vineland, NJ) and is further described in U.S. Pat. No. 4,895,452. Briefly, this device has a substantially cylindrical mixing chamber with at least one tangentially located inlet orifice. One or more orifices lead to a reservoir for the lipophilic phase, mixed with an oil phase if lipid-core paucilamellar lipid vesicles are to be formed, and at least one of the other orifices is attached to a reservoir for the aqueous phase. The different phases are driven into the cylindrical chamber through pumps, e.g., positive displacement pumps, and intersect in such a manner as to form a turbulent flow within the chamber. The paucilamellar lipid vesicles form rapidly, e.g., less than 1 second, and are removed from the chamber through an axially located discharge orifice. Preferably, there are four tangentially located inlet orifices and the lipid and aqueous phases are drawn from reservoirs, through positive displacement pumps, to alternating orifices. The fluid stream through the tangential orifices is guided in a spiral flow path from each inlet or injection orifice to the discharge orifice. The flow paths are controlled by the orientation or placement of the inlet or injection orifices so as to create a mixing zone by the intersection of the streams of liquid. The pump speeds, as well as the orifice and feed line diameters, are selected to achieve proper shear mixing for lipid vesicle formation. In most circumstances, turbulent flow is selected to provide adequate mixing.

No matter what device is used to form the paucilamellar lipid vesicles, if proper shear mixing is achieved they have a structure involving a large, unstructured amorphous center surrounded by a plurality of lipid bilayers having aqueous layers interspersed there between. About four lipid bilayers is standard with 2-8 possible. The amorphous center may be entirely filled with an aqueous material, e.g., a buffer and any aqueous material to be encapsulated, or may be partially or totally filled with an oily material, forming lipid-core paucilamellar lipid vesicles. If an aqueous center is used, the paucilamellar lipid vesicles will normally range in diameter from about 0.5-2µ while if an oily center is used, the size may increase to up to about 15-20µ depending upon the amount of oil used.

Use of Cyclodextin as a Carrier

Additionally, cyclodextrins are an alternate option for a collagen and/or HA carrier system into the dermis of the skin. Cyclodextrins are complex carbohydrates of 6, 7, or 8 D-glucopyranose residues that are linked by 1,4 glycosidic bonds. The three forms are dependent on the number of D-glucopyranose residues, the alpha form having 6, beta having 7, and gamma having 8. The alpha structure forms an annular ring with an internal hydrophobic cavity and a hydrophilic outer surface. Each cyclodextrin associates with a guest compound by fitting the compound into the hydrophobic cavity forming an inclusion complex. In this way cyclodextrins can be used as a delivery system to deliver a desired amount of material to a target location.

In one embodiment hydroxypropyl beta cyclodextrins can be used. Cyclodextrins are used because they have the ability to alter the physical, chemical, and biological properties of an associated guest compound through formation of the inclusion complex. This complex enhances the solubility, stability, and bioavailability of the guest compound so that the material can be isolated and used in a controlled delivery system. Formation an inclusion complex of collagen with an alpha-cyclodextrin allows for a targeted delivery system to the dermis.

The principal method for the isolation and purification of alpha-cyclodextrin takes advantage of its complex-forming ability. At completion of the reaction, 1-decanol is added to the reaction mixture to form an insoluble 1:1 alpha-cyelodextrin:1-decanol inclusion complex. The complex is continuously mixed with water and separated from the reaction mixture by centrifugation. The recovered complex is re-suspended in water and dissolved by heating. Subsequent cooling leads to re-precipitation of the complex. The precipitate is recovered by centrifugation, and 1-decanol is removed by steam distillation. Upon cooling, alpha-cyclodextrin crystallizes from solution. The crystals are removed by filtration and dried, yielding a white crystalline powder with a water content under 11%. The purity on a dried basis is at least 98%.

Dermatologically-Acceptable Carrier

The topical compositions of the present invention, in addition to the vesicle-contained collagen and/or HA, can further comprise a dermatologically acceptable carrier. A safe and effective amount of carrier is typically from about 50% to about 99.99%, preferably from about 80% to about 99.9%, more preferably from about 90% to about 98%, and even more preferably from about 90% to about 95% of the composition.

The carrier can be in a wide variety of forms. For example, emulsion carriers, including, but not limited to, oil-in-water, water-in-oil, water-in-oil-in-water, and oil-in-water-in-silicone emulsions, are useful herein.

Emulsions according to the present invention can contain a solution as described above and a lipid or oil. Lipids and oils may be derived from animals, plants, or petroleum and may be natural or synthetic (i.e., man-made). Preferred emulsions also contain a humectant, such as glycerin. Emulsions will preferably further contain from about 0.01% to about 10%, more preferably from about 0.1% to about 5%, of an emulsifier, based on the weight of the carrier. Emulsifiers may be nonionic, anionic or cationic. Suitable emulsifiers are disclosed in, for example, U.S. Pat. No. 3,755,560, issued Aug. 28, 1973 to Dickert et al.; U.S. Pat. No. 4,421,769, issued Dec. 20, 1983 to Dixon et al.; and *McCutcheon's Detergents and Emulsifiers*, North American Ed., pages 317-324 (1986).

The emulsion may also contain an anti-foaming agent to minimize foaming upon application to the epidermal tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, still more preferably about 5 centistokes or less.

Water-in-silicone emulsions can contain a continuous silicone phase and a dispersed aqueous phase. The continuous silicone phase exists as an external phase that contains or surrounds the discontinuous aqueous phase described hereinafter. The continuous silicone phase may contain one or more non-silicone oils. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

In emulsion technology, the term "dispersed phase" is a term well-known to one skilled in the art that means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such ingredients include thickeners, acids, bases, salts, chelants, gums, water-soluble or dispersible alcohols and polyols, buffers, preservatives, sunscreening agents, colorings, and the like.

Water-in-silicone emulsions can contain an emulsifier. In one embodiment, the composition contains from about 0.1% to about 10% emulsifier, more preferably from about 0.5% to about 7.5%, still more preferably from about 1% to about 5%, emulsifier by weight of the composition. The emulsifier helps disperse and suspend the aqueous phase within the continuous silicone phase.

Other topical carriers include oil-in-water emulsions, having a continuous aqueous phase and a hydrophobic, water-insoluble phase ("oil phase") dispersed therein. Examples of suitable oil-in-water emulsion carriers are described in U.S. Pat. No. 5,073,371, to Turner, D. J. et al., issued Dec. 17, 1991, and U.S. Pat. No. 5,073,372, to Turner, D. J. et al., issued Dec. 17, 1991.

An oil-in-water emulsion can contain a structuring agent to assist in the formation of a liquid crystalline gel network structure. Structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

In certain embodiments, oil-in-water emulsions that contain at least one hydrophilic surfactant which can disperse the hydrophobic materials in the water phase (percentages by weight of the topical carrier). The surfactant, at a minimum, must be hydrophilic enough to disperse in water. Among the nonionic surfactants that are useful herein are those that can be broadly defined as condensation products of long chain alcohols, e.g. C8-30 alcohols, with sugar or starch polymers, i.e., glycosides.

Other suitable surfactants useful herein include a wide variety of cationic, anionic, zwitterionic, and amphoteric surfactants such as are known in the art. See, e.g., McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety. The hydrophilic surfactants useful herein can contain a single surfactant, or any combination of suitable surfactants. The exact surfactant (or surfactants) chosen will depend upon the pH of the composition and the other components present.

Also useful herein are cationic surfactants, such as dialkyl quaternary ammonium compounds, examples of which are described in U.S. Pat. Nos. 5,151,209; 5,151,210; 5,120, 532; 4,387,090; 3,155,591; 3,929,678; 3,959,461; McCutcheon's, Detergents & Emulsifiers, (North American edition 1979) M.C. Publishing Co.; and Schwartz, et al., Surface Active Agents, Their Chemistry and Technology, New York: Interscience Publishers, 1949; which descriptions are incorporated herein by reference.

A wide variety of anionic surfactants are also useful herein. See, e.g., U.S. Pat. No. 3,929,678, to Laughlin et al., issued Dec. 30, 1975, which is incorporated herein by reference in its entirety. Nonlimiting examples of anionic surfactants include the alkoyl isethionates, and the alkyl and alkyl ether sulfates.

Examples of amphoteric and zwitterionic surfactants are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$-$C_{18}$) and one contains an anionic water solubilizing group, e.g., carboxy, sulfonate, sulfate, phosphate, or phosphonate.

The topical compositions of the subject invention, including but not limited to lotions and creams, may contain a dermatologically acceptable emollient. Such compositions preferably contain from about 1% to about 50% of the emollient. As used herein, "emollient" refers to a material useful for the prevention or relief of dryness, as well as for the protection of the skin. A wide variety of suitable emollients are known and may be used herein. Sagarin, Cosmetics, Science and Technology, 2nd Edition, Vol. 1, pp. 32-43 (1972), incorporated herein by reference, contains numerous examples of materials suitable as an emollient. A preferred emollient is glycerin. Glycerin is preferably used in an amount of from or about 0.001 to or about 30%, more preferably from or about 0.01 to or about 20%, still more preferably from or about 0.1 to or about 10%, e.g., 5%.

Creams are generally thicker than lotions due to higher levels of emollients or higher levels of thickeners.

Ointments of the present invention may contain a simple carrier base of animal or vegetable oils or semi-solid hydrocarbons (oleaginous); absorption ointment bases which absorb water to form emulsions; or water soluble carriers, e.g., a water soluble solution carrier. Ointments may further contain a thickening agent, such as described in Sagarin, Cosmetics, Science and Technology, 2nd Edition, Vol. 1, pp. 72-73 (1972), incorporated herein by reference, and/or an emollient. For example, an ointment may contain from about 2% to about 10% of an emollient; from about 0.1% to about 2% of a thickening agent; and the vesicle-collagen in the above described amounts.

Additional Skin Care Agents

The compositions of the present invention may contain one or more additional skin care agents, in addition to collagen and/or HA, the agents enumerated below do not include water unless specifically stated.

The additional agents should be suitable for application to epidermal tissue, that is, when incorporated into the composition they are suitable for use in contact with human epidermal tissue without undue toxicity, incompatibility, instability, allergic response, and the like. The CTFA Cosmetic Ingredient Handbook, Second Edition (1992) describes a wide variety of nonlimiting cosmetic and pharmaceutical ingredients commonly used in the skin care industry, which are suitable for use in the compositions of the present invention.

Examples of such ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof.

In any embodiment of the present invention, however, the agents useful herein can be categorized by the benefit they provide or by their postulated mode of action. However, it is to be understood that the additional agents for use herein can in some instances provide more than one benefit or operate via more than one mode of action. Therefore, classifications herein are made for the sake of convenience and are not intended to limit the agent to that particular application or applications listed.

Desquamation Agents

A safe and effective amount of a desquamation agent may be added to the compositions of the present invention, more preferably from about 0.1% to about 10%, even more preferably from about 0.2% to about 5%, also preferably from about 0.5% to about 4%, by weight of the composition. Desquamation agents enhance the skin appearance benefits of the present invention. For example, the desquamation agents tend to improve the texture of the skin (e.g., smoothness). One desquamation system that is suitable for use herein contains sulfhydryl compounds and zwitterionic surfactants and is described in U.S. Pat. No. 5,681,852, to Bissett, incorporated herein by reference. Another desquamation system that is suitable for use herein contains salicylic acid and zwitterionic surfactants and is described in U.S. Pat. No. 5,652,228 to Bissett, incorporated herein by reference. Zwitterionic surfactants such as described in these applications are also useful as desquamatory agents herein, with cetyl betaine being particularly preferred.

Anti-Acne Agents

The compositions of the present invention may contain a safe and effective amount of one or more anti-acne agents. Examples of useful anti-acne agents include resorcinol, sulfur, salicylic acid, benzoyl peroxide, erythromycin, zinc, etc. Further examples of suitable anti-acne agents are described in further detail in U.S. Pat. No. 5,607,980, issued to McAtee et al, on Mar. 4, 1997.

Anti-Wrinkle Agents/Anti-Atrophy Agents

The compositions of the present invention may further contain a safe and effective amount of one or more anti-wrinkle agents or anti-atrophy agents. Exemplary anti-wrinkle/anti-atrophy agents suitable for use in the compositions of the present invention include sulfur-containing D and L amino acids and their derivatives and salts, particularly the N-acetyl derivatives, a preferred example of which is N-acetyl-L-cysteine; thiols, e.g. ethane thiol; hydroxy acids (e.g., alpha-hydroxy acids such as lactic acid and glycolic acid or beta-hydroxy acids such as salicylic acid and salicylic acid derivatives such as the octanoyl derivative), phytic acid, lipoic acid; lysophosphatidic acid, skin peel agents (e.g., phenol and the like), vitamin $B_3$ compounds, retinoids, and hyaluronic acid, which enhance the epidermal tissue appearance benefits of the present invention, especially in regulating epidermal tissue condition, e.g., skin condition.

Vitamin $B_3$ Compounds

The compositions of the present invention may contain a safe and effective amount of a vitamin $B_3$ compound. Vitamin $B_3$ compounds are particularly useful for regulating skin condition as described in U.S. application Ser. No. 08/834,010, filed Apr. 11, 1997 (corresponding to international publication WO 97/39733 A1, published Oct. 30, 1997). Examples of suitable vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.). The vitamin compounds may be included as the substantially pure material, or as an extract obtained by suitable physical and/or chemical isolation from natural (e.g., plant) sources.

Retinoids

The compositions of the present invention may also contain a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and U.S. Pat. No. Reissue 34,075, issued Sep. 22, 1992 to Purcell et al. Other suitable retinoids are tocopherylretinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof.

Hydroxy Acids

The compositions of the present invention may contain a safe and effective amount of a hydroxy acid. Preferred hydroxy acids for use in the compositions of the present invention include salicylic acid and salicylic acid derivatives.

Anti-Oxidants/Radical Scavengers

The compositions of the present invention may include a safe and effective amount of an anti-oxidant/radical scavenger. The anti-oxidant/radical scavenger is especially useful for providing protection against UV radiation which can cause increased scaling or texture changes in the stratum corneum and against other environmental agents which can cause skin damage.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pidolate, nordihydroguaiaretic acid, bioflavonoids, curcumin, lysine, methionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee.

Chelators

The compositions of the present invention may also contain a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. Preferred chelators useful in compositions of the subject invention are furildioxime, furilmonoxime, and derivatives thereof Flavonoids The compositions of the present invention may optionally contain a flavonoid compound. Flavonoids are broadly disclosed in U.S. Pat. Nos. 5,686,082 and 5,686,367, both of which are herein incorporated by reference. Flavonoids suitable for use in the present invention are flavanones selected from unsubstituted flavanones, mono-substituted flavanones, and mixtures thereof chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1-C8 alkyl, C1-C4 alkoxyl, 0-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and trihydroxy chalcones (e.g., 2',3',4'-trihydroxy chalcone, 4,2', 4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

Preferred for use herein are unsubstituted flavanone, methoxy flavanones, unsubstituted chalcone, 2',4-dihydroxy chalcone, and mixtures thereof. More preferred are unsubstituted flavanone, unsubstituted chalcone (especially the trans isomer), and mixtures thereof.

They can be synthetic materials or obtained as extracts from natural sources (e.g., plants). The naturally sourced material can also further be derivatized (e.g., an ester or ether derivative prepared following extraction from a natural source). Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.).

Anti-Inflammatory Agents

A safe and effective amount of an anti-inflammatory agent may be added to the compositions of the present invention, preferably from about 0.1% to about 10%, more preferably from about 0.5% to about 5%, of the composition. The anti-inflammatory agent enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chloroprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, one may refer to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology, 1, R. A. Scherrer, et al., Academic Press, New York (1974).

Specific non-steroidal anti-inflammatory agents useful in the composition invention include, but are not limited to:
1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and
6) the pyrazoles, such as phenylbutazone, oxyphenbutazone, feprazone, azapropazone, and trimethazone.

Mixtures of these non-steroidal anti-inflammatory agents may also be employed, as well as the dermatologically acceptable salts and esters of these agents. For example, etofenamate, a flufenamic acid derivative, is particularly useful for topical application. Of the nonsteroidal anti-inflammatory agents, ibuprofen, naproxen, flufenamic acid, etofenamate, aspirin, mefenamic acid, meclofenamic acid, piroxicam and felbinac are preferred; ibuprofen, naproxen, ketoprofen, etofenamate, aspirin and flufenamic acid are more preferred.

Finally, so-called "natural" anti-inflammatory agents are useful in methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, and sea whip extract, may be used.

Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$ saturated or unsaturated esters of the acids, preferably $C_{10}$-$C_{24}$, more preferably $C_{16}$-$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

Anti-Cellulite Agents

The compositions of the present invention may also contain a safe and effective amount of an anti-cellulite agent. Suitable agents may include, but are not limited to, xanthine compounds (e.g., caffeine, theophylline, theobromine, and aminophylline).

Topical Anesthetics

The compositions of the present invention may also contain a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Tanning Agents

The compositions of the present invention may contain a tanning agent. When present, it is preferable that the compositions contain from about 0.1% to about 20%, more preferably from about 2% to about 7%, and still more preferably from about 3% to about 6%, by weight of the composition, of dihydroxyacetone as an artificial tanning agent.

Skin Lightening Agents

The compositions of the present invention may contain a skin lightening agent. When used, the compositions preferably contain from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, ascorbic acid and derivatives thereof (e.g., magnesium ascorbyl phosphate or sodium ascorbyl phosphate), and extracts (e.g., mulberry extract, placental extract). Skin lightening agents suitable for use herein also include those described in the PCT publication No. 95/34280, in the name of Hillebrand, corresponding to PCT Application No. U.S. 95/07432, filed Jun. 12, 1995; and co-pending U.S. application Ser. No. 08/390,152 filed in the names of Kvalnes, Mitchell A. DeLong, Barton J. Bradbury, Curtis B. Motley, and John D. Carter, corresponding to PCT Publication No. 95/23780, published Sep. 8, 1995.

Skin Soothing and Skin Healing Agents

The compositions of the present invention may comprise a skin soothing or skin healing agent. Skin soothing or skin healing agents suitable for use herein include panthenoic acid derivatives (including panthenol, dexpanthenol, ethyl panthenol), aloe vera, allantoin, bisabolol, and dipotassium glycyrrhizinate. A safe and effective amount of a skin soothing or skin healing agent may be added to the present composition, preferably, from about 0.1% to about 30%, more preferably from about 0.5% to about 20%, still more preferably from about 0.5% to about 10%, by weight of the composition formed.

Antimicrobial and Antifungal Agents

The compositions of the present invention may contain an antimicrobial or antifungal agent, Such agents are capable of destroying microbes, preventing the development of microbes or preventing the pathogenic action of microbes. A safe and effective amount of an antimicrobial or antifungal agent may be added to the present compositions, preferably, from about 0.001% to about 10%, more preferably from about 0.01% to about 5%, and still more preferably from about 0.05% to about 2%.

Examples of antimicrobial and antifungal agents include B-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachloro-meta xylenol, nystatin, tolnaftate, zinc pyrithione and clotrimazole.

Additionally antimicrobial peptides can be used.

Sunscreen Agents

Exposure to ultraviolet light can result in excessive scaling and texture changes of the stratum corneum. Therefore, the compositions of the subject invention may optionally contain a sunscreen agent. As used herein, "sunscreen agent" includes both sunscreen agents and physical sunblocks. Suitable sunscreen agents may be organic or inorganic.

Inorganic sunscreens useful herein include the following metallic oxides; titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. When used herein, the inorganic sunscreens are present in the amount of from about 0.1% to about 20%, preferably from about 0.5% to about 10%, more preferably from about 1% to about 5%, by weight of the composition.

A wide variety of conventional organic sunscreen agents are suitable for use herein. Sagarin, et al., at Chapter VIII, pages 189 et seq., of Cosmetics Science and Technology (1972), discloses numerous suitable agents. Specific suitable sunscreen agents include, for example: p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylacetoumbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4, 4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one), terephthalylidene dicamphor sulfonic acid and 4-isopropyl-di-benzoylmethane.

Conditioning Agents

The compositions of the present invention may contain a conditioning agent selected from humectants, moisturizers, or skin conditioners. A variety of these materials can be employed and each can be present at a level of from about 0.01% to about 20%, more preferably from about 0.1% to about 10%, and still more preferably from about 0.5% to about 7% by weight of the composition. These materials include, but are not limited to, guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fucose, glucosamine); hyaluronic acid; lactamide monoethanolamine; acetamide monoethanolamine; panthenol; allantoin; and mixtures thereof. Also useful herein are the propoxylated glycerols described in U.S. Pat. No. 4,976,953, to Orr et al, issued Dec. 11, 1990.

Structuring Agents

The compositions hereof, and especially the emulsions hereof, may contain a structuring agent. Structuring agents are particularly preferred in the oil-in-water emulsions of the present invention. Without being limited by theory, it is believed that the structuring agent assists in providing rheological characteristics to the composition which contribute to the stability of the composition. For example, the structuring agent tends to assist in the formation of the liquid crystalline gel network structures. The structuring agent may also function as an emulsifier or surfactant. Preferred compositions of this invention contain from about 0.1% to about 20%, more preferably from about 0.1% to about 10%, still more preferably from about 0.5% to about 9%, of one or more structuring agents.

The preferred structuring agents of the present invention are selected from stearic acid, palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, and mixtures thereof.

Thickening Agent (Including Thickeners and Gelling Agents)

The compositions of the present invention can contain one or more thickening agents, preferably from about 0.1% to about 5%, more preferably from about 0.1% to about 4%, and still more preferably from about 0.25% to about 3%, by weight of the composition.

Nonlimiting classes of thickening agents for use in the compositions of the invention include those selected from the following: carboxylic acid polymers (such as those described in U.S. Pat. No. 5,087,445, to Haffey et al, issued Feb. 11, 1992; U.S. Pat. No. 4,509,949, to Huang et al, issued Apr. 5, 1985; U.S. Pat. No. 2,798,053, to Brown, issued Jul. 2, 1957; and in CTFA International Cosmetic Ingredient Dictionary, Fourth Edition, 1991, pp. 12 and 80); crosslinked polyacrylate polymers (such as those described in U.S. Pat. No. 5,100,660, to Hawe et al, issued Mar. 31, 1992; U.S. Pat. No. 4,849,484, to Heard, issued Jul. 18, 1989; U.S. Pat. No. 4,835,206, to Farrar et al, issued May 30, 1989; U.S. Pat. No. 4,628,078 to Glover et al issued Dec. 9, 1986; U.S. Pat. No. 4,599,379 to Flesher et al issued Jul. 8, 1986; and EP 228,868, to Farrar et al, published Jul. 15, 1987); polyacrylamide polymers (such as nonionic polyacrylamide polymers including substituted branched or unbranched polymers and multi-block copolymers of acrylamides and substituted acrylamides with acrylic acids and substituted acrylic acids); polysaccharides (which refers to gelling agents that contain a backbone of repeating sugar (i.e., carbohydrate) units, including cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof); and gums (such as acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboyxmethyl dextran, sodium carrageenan, tragacanth gum, xanthan gum, and mixtures thereof).

Composition Preparation

The compositions useful for the methods of the present invention are generally prepared by conventional methods such as are known in the art of making topical compositions. Such methods typically involve mixing of the ingredients in one or more steps to a relatively uniform state, with or without heating, cooling, application of vacuum, and the like.

Preservatives

Preservatives can be incorporated into the compositions of the present invention to protect against the growth of potentially harmful microorganisms. While it is in the aqueous phase that microorganisms tend to grow, microorganisms can also reside in the anhydrous or oil phase. As such, preservatives, which have solubility in both water and oil, are preferably employed in the present compositions. Suitable traditional preservatives for compositions of this invention are alkyl esters of parahydroxybenzoic acid. Other preservatives, which can be used include hydantoin derivatives, propionate salts, and a variety of quaternary ammonium compounds.

Particularly preferred preservatives are methylparaben, imidazolidinyl urea, sodium dehydroacetate, propylparaben, trisodium ethylenediamine tetraacetate (EDTA), and benzyl alcohol. The preservative can be selected to avoid possible incompatibilities between the preservative and other ingredients. Preservatives are preferably employed in amounts ranging from about 0.01% to about 2% by weight of the composition. Other preservatives known in the art can be used in the present invention.

Methods of Administration

Another aspect of the invention is to provide a method of administering a composition of the invention, wherein dispersed lipid vesicles and/or cyclodextrins comprising collagen are provided to the dermal layer of a patient's skin. The method includes the step of contacting the skin or other target site of the subject with a composition including a lipid vesicle (e.g., non-phospholipid paucilamellar lipid vesicle) having a cavity containing human collagen.

The compositions of the present invention are useful for regulating and/or improving mammalian skin condition. Such regulation of epidermal tissue conditions can include prophylactic and therapeutic regulation. For example, such regulating methods are directed to thickening dermal tissue and preventing and/or retarding atrophy of mammalian skin, preventing and/or retarding the appearance of spider vessels and/or red blotchiness on mammalian skin, preventing and/or retarding the appearance of dark circles under the eye of a mammal, preventing and/or retarding sallowness of mammalian skin, preventing and/or retarding sagging of mammalian skin, softening and/or smoothing lips of a mammal, preventing and/or relieving itch of mammalian skin, regulating skin texture (e.g. wrinkles and fine lines), and improving skin color (e.g. redness, freckles).

Regulating epidermal tissue condition involves topically applying to the epidermal tissue a safe and effective amount of a composition of the present invention. The amount of the composition which is applied, the frequency of application and the period of use will vary widely depending upon the level of collagen (and, when present, other skin care agents) of a given composition and the level of regulation desired, e.g., in light of the level of epidermal tissue damage present or expected to occur.

In a preferred embodiment, the composition is chronically applied to the skin. By "chronic topical application" is meant continued topical application of the composition over an extended period during the subject's lifetime, preferably for a period of at least about one week, more preferably for a period of at least about one month, even more preferably for at least about three months, even more preferably for at least about six months, and more preferably still for at least about one year. While benefits are obtainable after various maximum periods of use (e.g., five, ten or twenty years), it is preferred that chronic application continue throughout the subject's lifetime. Typically applications would be on the order of about once per day over such extended periods, however application rates can vary from about once per week up to about three times per day or more.

A wide range of quantities of the compositions of the present invention can be employed to provide a skin appearance and/or feel benefit. Quantities of the present compositions which are typically applied per application are, in mg composition/cm$^2$ skin, from about 0.1 mg/cm$^2$ to about 10 mg/cm$^2$. A particularly useful application amount is about 1 mg/cm$^2$ to about 2 mg/cm$^2$.

Improving and/or regulating epidermal tissue condition is preferably practiced by applying a composition in the form of a skin lotion, cream, gel, foam, ointment, paste, emulsion, spray, conditioner, tonic, cosmetic, lipstick, foundation, after-shave, or the like which is preferably intended to be left on the skin or other keratin structure for some esthetic, prophylactic, therapeutic or other benefit (i.e., a "leave-on" composition). After applying the composition to the skin, it is preferably left on the skin for a period of at least about 15 minutes, more preferably at least about 30 minutes, even more preferably at least about 1 hour, still more preferably for at least several hours, e.g., up to about 12 hours. Any part of the external portion of the body can be treated, e.g., lips, under-eye area, eyelids, scalp, neck, torso, arms, hands, legs, feet, etc. The composition can be applied with the fingers or with an implement or device (e.g., pad, cotton ball, applicator pen, spray applicator, and the like).

Another approach to ensure a continuous dispersal of at least a minimum level of collagen (and, when present, at least one skin care agent) to the dermal layer is to apply the compound by use of a patch applied, e.g., to the face. Such an approach is particularly useful for problem skin areas needing more intensive treatment (e.g., facial crows feet area, frown lines, under eye area, and the like). The patch can be occlusive, semi-occlusive or non-occlusive and can be adhesive or non-adhesive. The composition can be contained within the patch or be applied to the skin prior to application of the patch. The patch can also include additional agents such as chemical initiators for exothermic reactions such as those described in U.S. Pat. Nos. 5,821,250, 5,981,547, and 5,972,957 to Wu, et al. The patch is preferably left on the skin for a period of at least about 5 minutes, more preferably at least about 15 minutes, more preferably still at least about 30 minutes, even more preferably at least about 1 hour, still more preferably at night as a form of night therapy.

Example 1—Absorption of Collagen into Skin

The study evaluated the percutaneous absorption pharmacokinetics of $^{14}$C-Collagen spiked to a liposome. Absorption was measured in excised human face skin, in vitro, using the finite dose technique and Franz Diffusion Cells.

The in vitro human cadaver skin model has proven to be a valuable tool for the study of percutaneous absorption and the determination of the pharmacokinetics of topically applied drugs. The model uses human cadaver skin mounted in specially designed diffusion cells that allow the skin to be maintained at a temperature and humidity that match typical in vivo conditions. A finite dose (e.g. 4-7 mg/cm$^2$) of formulation is applied to the outer surface of the skin and drug absorption is measured by monitoring its rate of appearance in the receptor solution bathing the inner surface of the skin.

Test Article - Day Cream
Tracer - $^{14}$C Collagen (ARC 2005) (methyl-14C)

The product was tested on replicate skin sections from three different skin donors, for the percutaneous absorption of $^{14}$C-Collagen spiked formulation over a 48-hour dose period. At pre-selected times after dosing, the dermal reservoir solution was removed in its entirety, replaced with fresh receptor solution, and an aliquot saved for subsequent analysis. At the completion of the study, the dermal and epidermal contents were also evaluated. The samples were analyzed for $^{14}$C isotope content by liquid scintillation spectroscopy.

SUMMARY TABLE

[¹⁴C]-Collagen spiked Novasome Total Absorption Results Across Donor Percutaneous Absorption of ¹⁴C-Collagen as radioisotope through Excised Human Face Skin over 48 hours from a Single Application. Mean ± SE (n = 3) as Total Mass (μg) and Percent of Applied Dose

| Skin Source | Total Pen* (μg) | Total Pen (%) |
|---|---|---|
| Eyelid | 3.83 ± 2.40 | 42.96 ± 21.21 |
| Pre-Auricular | 2.63 ± 0.56 | 19.63 ± 1.27 |
| Combined Data | 3.03 ± 0.51 | 27.40 ± 7.81 |

*"Pen" is penetration

The radiolabeled collagen was prepared by American Radiolabeled Chemicals, Inc. (ARC; St. Louis, MO 63143). Briefly, the study Sponsor sent their collagen to ARC for labeling. ARC labeled the collagen by methylation using [¹⁴C] formaldehyde and sodium cyanoborohydride. The radiolabeled material was indicated to have a specific activity of 25 μCi/mg and was provided in a 1 mL volume of 0.01M potassium phosphate buffer (pH 7.2).

The radiolabeled material was first dried by vacuum centrifugation (Speed Vac, Savant, Inc.) for approximately 3 hours, followed by reconstitution in 50 μl, of the Novasome Day Cream and mixed by dual syringe (100 μL) cross extrusion through a 3-way stop-cock valve 20 times. The spiked cream was allowed to equilibrate for 24 hrs at room temperature prior to use. Final specific activity was measured as 0.1 μCi/μL cream formulation with 3.82 μg/uL radiolabeled collagen contributing to the cream base.

Study Skin Preparation:

Human excised face skin (eyelid and pre-auricular) without obvious signs of skin disease, obtained following cosmetic surgery, was used in this study. It was cleared of all subcutaneous tissue and the lower ~25% of the dermis, sealed in water-impermeable plastic bags and stored at ≤−70° C. until used. Prior to the experiment, skin was thawed, and then rinsed in water to remove any adherent blood or other material from the surface.

Skin from a single donor was cut into multiple smaller sections large enough to fit on Franz diffusion cells (0.4 cm²-0.8 cm²). The dermal chamber was filled to capacity with a reservoir solution of phosphate-buffered isotonic saline (PBS), pH 7.4±0.1, and the epidermal chamber was left open to the ambient laboratory environment. The cells were then placed in a diffusion apparatus in which the dermal reservoir solution was stirred magnetically at approximately 600 RPM and its skin surface temperature maintained at 32.0°±1.0° C.

To assure the integrity of each skin section, its permeability to tritiated water was determined before application of the test products. Following a brief (0.5-1 hour) equilibrium period, ³H₂O (NEN, Boston, MA, sp. Act.~0.5 μCi/mL) was layered across the top of the skin by dropper so that the entire exposed surface was covered (approximately 100-500 μL). After 5 minutes the ³H₂O aqueous layer was removed. At 30 minutes the receptor solution was collected and analyzed for radioactive content by liquid scintillation counting. Following the integrity test the receptor solution was changed multiple times to remove any measurable residual tritium.

Dosing and Sample Collection

Prior to administration of the topical test formulations to the skin sections, the chimney was removed from the Franz Cell to allow full access to the epidermal surface of the skin and the reservoir solution was replaced with a fresh solution of PBS.

Subsequently, the test product was applied to replicate sections of the same donor skin. Dosing was performed using a positive displacement pipette set to deliver 5 μL formulations/cm². Given the available skin, three chamber sizes with different dosing area were using (0.4, 0.5 and 0.8 cm²). The dose was spread throughout the surface with the tip of the pipette. Five to ten minutes after application the chimney portion of the Franz Cell was replaced. Spare cells were not dosed, but sampled, to evaluate for interfering substances during the analytical analysis.

At pre-selected time intervals after test formulation application (0.5, 1, 3, 7, 19, 26, 43, 48 hr) the receptor solution was removed in its entirety replaced with fresh solution, and an aliquot taken for analysis.

After the last sample was collected, the surface of the skin was washed with double distilled de-ionized water to collect un-absorbed formulation form the surface of the skin. Following the wash, the skin was removed from the chamber, separated into epidermis and dermis, and each processed for subsequent analysis for isotope content.

Analytical Methods

Analysis for ¹⁴C-isotope content of each sample was by liquid scintillation spectroscopy. One-milliliter volumes of each receptor solution and each surface wash solution received 5-7 mL scintillation fluid. Tissue (epidermis and dermis) was dissolved in Soluene-350 (PerkinElmer; Lot #24-060203) overnight, following which each sample received 5-7 mL of scintillation fluid.

Samples were quantified for ¹⁴C content by liquid scintillation spectroscopy using a PerkinElmer Tri-Garb 3100TR liquid scintillation counter. Each sample was counted for no less than 5 minutes each, in duplicate. Counts per minute (CPM) were automatically converted to decays per minute (DPM) using the external standard quench correction method. All data were corrected for isotope background from blank samples.

TABLE 1

Rate of Penetration as Mean Flux (μg/cm²/hr) Results Percutaneous Absorption of ¹⁴C-Collagen as radioisotope through over 48 hours from a Single Application Human Cadaver Skin (Mean ± SD Eyelid, Mean ± SE Pre-Auricular, n = 1-2 Donors).

| Time (hr)* | Eyelid | Pre-Auricular | Combined Data |
|---|---|---|---|
| 0.25 | 0.14 ± 0.10 | 0.04 ± 0.02 | 0.07 ± 0.04 |
| 0.75 | 0.20 ± 0.02 | 0.12 ± 0.00 | 0.15 ± 0.03 |
| 2.0 | 0.18 ± 0.01 | 0.15 ± 0.06 | 0.16 ± 0.03 |
| 5.0 | 0.21 ± 0.09 | 0.10 ± 0.04 | 0.14 ± 0.04 |
| 13.0 | 0.17 ± 0.07 | 0.07 ± 0.01 | 0.11 ± 0.03 |
| 22.5 | 0.23 ± 0.18 | 0.08 ± 0.00 | 0.13 ± 0.05 |
| 35.0 | 0.10 ± 0.01 | 0.07 ± 0.00 | 0.08 ± 0.01 |
| 45.5 | 0.30 ± 0.30 | 0.07 ± 0.01 | 0.15 ± 0.08 |

*Time as midpoint between samples.

TABLE 2

Total Absorption and Mass Balance Results Percutaneous Absorption of ¹⁴C-Collagen as radioisotope through Human Cadaver Skin over 48 hours from a Single Application. Mean ± SD Eyelid, and Mean ± SE Pre-Auricular as Percent of Applied Dose and Total Mass (μg). (n = 1-2 Donors)

| Parameter | Eyelid | Pre-Auricular | Combined Data |
|---|---|---|---|
| Total Absorption (μg) | 3.83 ± 2.40 | 2.63 ± 0.56 | 3.03 ± 0.51 |
| Dermis (μg) | 0.02 ± 0.01 | 0.03 ± 0.01 | 0.02 ± 0.01 |
| Epidermis (μg) | 0.13 ± 0.06 | 0.28 ± 0.13 | 0.23 ± 0.09 |

TABLE 2-continued

Total Absorption and Mass Balance Results
Percutaneous Absorption of $^{14}$C-Collagen as radioisotope through
Human Cadaver Skin over 48 hours from a Single Application.
Mean ± SD Eyelid, and Mean ± SE Pre-Auricular as Percent of
Applied Dose and Total Mass (μg). (n = 1-2 Donors)

| Parameter | Eyelid | Pre-Auricular | Combined Data |
|---|---|---|---|
| Surface Wash (μg) | 5.37 ± 0.25 | 9.73 ± 1.65 | 8.28 ± 1.74 |
| Total Absorption (5) | 42.96 ± 21.21 | 19.63 ± 1.27 | 27.40 ± 7.81 |
| Dermis (%) | 0.20 ± 0.11 | 0.18 ± 0.03 | 0.19 ± 0.02 |
| Epidermis (%) | 1.51 ± 0.48 | 2.01 ± 0.66 | 1.84 ± 0.42 |
| Surface Wash (%) | 63.14 ± 7.04 | 74.10 ± 0.48 | 70.45 ± 3.67 |
| Total Recovery (%) | 107.81 ± 14.76 | 95.92 ± 2.44 | 99.88 ± 4.21 |

The data indicated that when $^{14}$C-Collagen is incorporated into the Novasome Day Cream base formulation, radioisotope penetrates into and through human excised face skin.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

I claim:

1. A liposome having encapsulated therein collagen having a particle size of about 20 to 150 nm and linear cross-linked hyaluronic acid of less than 500 kDa, wherein the liposome is a non-phospholipid paucilamellar liposome that is about 50 to 700 nm in size.

2. The liposome, according to claim 1, wherein the collagen is human collagen.

3. The liposome, according to claim 1, wherein the collagen is a recombinant collagen.

4. The liposome, according to claim 1, wherein said collagen is in the fibril form.

5. The liposome, according to claim 1, further comprising at least one of the group consisting of desquamation agents, anti-acne agents, anti-wrinkle agents, vitamin B3 compounds, retinoids, hydroxyl acids, anti-oxidants, chelators, flavonoids, anti-inflammatory agents, anti-cellulite agents, topical anesthetics, tanning agents, skin lightening agents, skin soothing agents, antimicrobial agents, sunscreen agents, conditioning agents, thickening agent, and preservatives.

6. A method for administering collagen and hyaluronic acid into the skin of a subject, the method comprising the step of contacting the skin of the subject with a composition comprising a liposome of claim 1.

7. The method, according to claim 6, wherein the liposome further comprises at least one of the group consisting of desquamation agents, anti-acne agents, anti-wrinkle agents, vitamin B3 compounds, retinoids, hydroxyl acids, anti-oxidants, radical scavengers, chelators, flavonoids, anti-inflammatory agents, anti-cellulite agents, topical anesthetics, tanning agents, skin lightening agents, skin soothing agents, antimicrobial and antifungal agents, sunscreen agents, conditioning agents, thickening agents, and preservatives.

* * * * *